US008145308B2

(12) United States Patent
Sambelashvili et al.

(10) Patent No.: US 8,145,308 B2
(45) Date of Patent: Mar. 27, 2012

(54) METHOD AND APPARATUS FOR DETERMINING A PARAMETER ASSOCIATED WITH DELIVERY OF THERAPY IN A MEDICAL DEVICE

(75) Inventors: Aleksandre T Sambelashvili, Maple Grove, MN (US); Thomas J Mullen, Andover, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 794 days.

(21) Appl. No.: 12/047,951

(22) Filed: Mar. 13, 2008

(65) Prior Publication Data

US 2009/0234415 A1 Sep. 17, 2009

(51) Int. Cl.
*A61N 1/368* (2006.01)
(52) U.S. Cl. .......... 607/25; 607/9; 607/11; 607/17; 607/27; 607/28; 607/115; 607/116; 607/119
(58) Field of Classification Search ............ 607/9, 11, 607/17, 25, 27–28, 115–116, 119
See application file for complete search history.

(56) References Cited

U.S. PATENT DOCUMENTS

| | | | |
|---|---|---|---|
| 6,393,316 B1 | 5/2002 | Gillberg et al. | |
| 6,871,096 B2 | 3/2005 | Hill | |
| 7,113,823 B2 | 9/2006 | Yonce et al. | |
| 7,254,442 B2 | 8/2007 | Van Gelder et al. | |
| 2003/0204214 A1 | 10/2003 | Ferek-Patric | |
| 2005/0137638 A1 | 6/2005 | Yonce et al. | |
| 2006/0224198 A1 | 10/2006 | Dong et al. | |
| 2007/0078489 A1 | 4/2007 | Meyer et al. | |
| 2007/0239053 A1 | 10/2007 | Bhunia | |

FOREIGN PATENT DOCUMENTS

| | | |
|---|---|---|
| EP | 1 430 931 | 6/2004 |
| EP | 1 529 551 | 5/2005 |

OTHER PUBLICATIONS

PCT International Search report, PCT/US09/036032, 3 pages.
Lorella Gianfranchi et al., "Fusion beat in patients with heart failure treated with left ventricular pacing: may ECG morphology relate to mechanical synchrony? A pilot study", *Cardiovascular Ultrasound*, Biomed Central, London, GB, vol. 6, No. 1, Jan. 1, 2008, pp. 1-9.

*Primary Examiner* — Carl H Layno
*Assistant Examiner* — Deborah Malamud
(74) *Attorney, Agent, or Firm* — Reed A. Duthler; Stephen W. Bauer

(57) ABSTRACT

A medical device and method for determining a parameter for delivery of a predetermined pacing therapy that includes a plurality of electrodes to deliver a pacing therapy, including the predetermined pacing therapy, and a control unit to control the timing of the delivery of the pacing therapy, including the predetermined pacing therapy, by the electrodes. A processor generates a first template in response to the pacing therapy being delivered to only one of a right ventricle and a left ventricle, and a second template in response to the pacing therapy being delivered to only the other of the right ventricle and the left ventricle, and determines the parameter in response to a comparing of subsequently delivered pacing therapy to the first template and the second template.

20 Claims, 6 Drawing Sheets

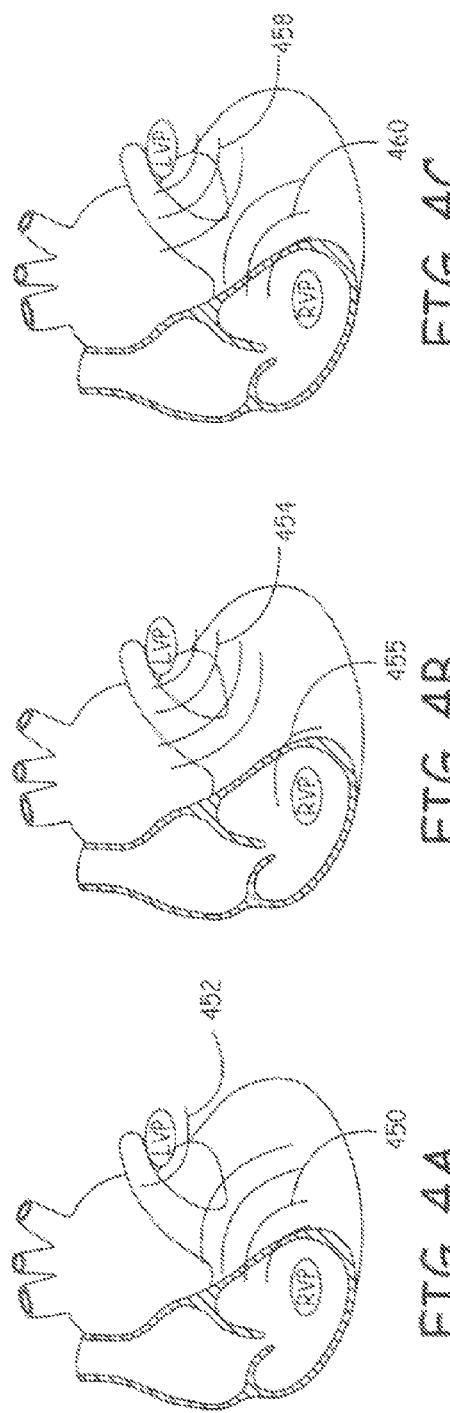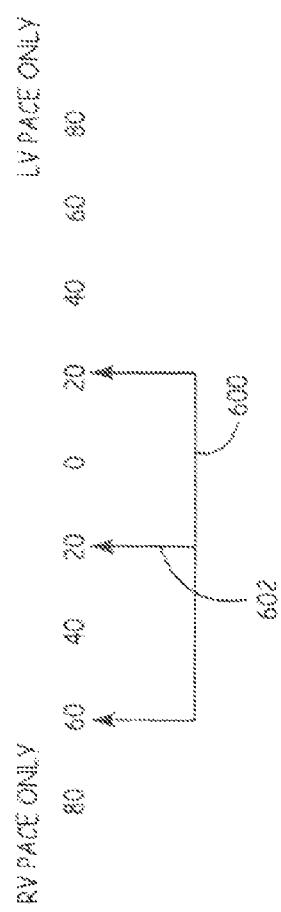

METHOD AND APPARATUS FOR DETERMINING A PARAMETER ASSOCIATED WITH DELIVERY OF THERAPY IN A MEDICAL DEVICE

FIELD

The discussion relates to cardiac pacing systems, and more particularly, to an apparatus and method for determining cardiac function for heart failure patients.

BACKGROUND

Heart failure affects approximately 5 million people in the United States. Many moderate to severe heart failure patients may also have a condition in which the two lower chambers of the heart (known as the left and right ventricles) are not beating together as they do normally. In medical terms, this condition is called "ventricular dysynchrony." Ventricular dysynchrony disturbs the synchronous beating of the heart, and as a result the heart does not adequately pump blood to meet the needs of the body. More specifically, ventricular dysynchrony typically results from intraventricular conduction delays iii(IVCD) that disturb the synchronous beating of the ventricles. Typically, the IVCD has a left bundle branch block (LBBB) morphology.

One therapy to treat left ventricle dysynchrony is cardiac resynchronization therapy (CRT), which, when used in combination with stable, optimal medical therapy, is designed to reduce symptoms by restoring the sequence of electrical and mechanical ventricular activation. Cardiac resynchronization therapy (CRT) provides atrial-synchronized, biventricular pacing using standard pacing technology combined with a special third lead implanted via the coronary sinus and positioned in a cardiac vein to sense and pace the left ventricle. Following a sensed atrial contraction, both ventricles are stimulated to contract more synchronously. The resulting resynchronization of ventricular contraction reduces mitral regurgitation and optimizes left ventricular filling and ejection, thereby improving cardiac function.

Currently available CRT bi-ventricular pacing generally employs one lead positioned in operative communication with the right ventricle (RV) and one lead in operative communication with a portion of one of the tributaries of the coronary venous system. The myocardial venous system provides a pathway for deployment of a left ventricular stimulation lead (and associated electrodes) to operatively communicate with the left ventricle. In most patients, an additional lead is deployed to the right atrium (RA) for atrioventricular (AV) synchronization during pacing. Exceptions for placement of the atrial lead include patients suffering from chronic atrial fibrillation (AF) or having a relatively high AF "burden." According to such CRT delivery, electrical stimulation of both the right and left ventricle operates to assist ventricular asynchrony and increase contractility, as measured by ventricular pressure development (dP/dt). For certain patients, further assistance of contractility can be achieved by variation of the inter-ventricular interval.

The timing between atrial and ventricular pacing is determined by the programmed value of the atrio-ventricular (AV) delay. The timing between right- and left-ventricular pacing pulses is determined by the programmed value of the inter-ventricular (VV) delay. Several acute studies have demonstrated a significant correlation of cardiac function to programmed values of atrioventricular (AV) and interventricular (VV) delays. While AV delay optimization is primarily focused on ensuring synchrony of the atrial and ventricular contractions, the goal of VV delay optimization is to decrease intraventricular mechanical dyssynchrony. Since there is a link between electrical and mechanical activation of the left ventricle during biventricular pacing, decreasing electrical dyssynchrony typically improves left ventricular mechanical function. In order to achieve the greatest improvement in left ventricular contractility, it is desirable to determine an interventricular time delay that corresponds to the maximal electrical synchrony of the left ventricle, known as the optimal VV delay.

When both the left and right ventricular pacing pulses contribute to left ventricular activation, electrical fusion of the two paced wavefronts occurs. The range of VV delays where fusion of the two paced wavefronts can be observed is termed the biventricular pacing window (also called the fusion band). This range may vary from patient to patient and may also be dependent on lead location, conduction disorder, and scar location.

Current methods for determining VV optimization require the use of echocardiography to evaluate the filling, cardiac output, and degree of ventricular dyssynchrony that occurs for different VV settings. Unfortunately, determinations of optimal VV delay settings using echocardiography are time consuming and typically require a burdensome amount of clinical resources. Therefore, what is needed is an improved method and apparatus for determining an optimal VV delay necessary to efficiently and chronically deliver and control a pacing therapy to effect ventricular fusion associated with bi-ventricular CRT pacing therapy.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein:

FIGS. 4A to 4C are schematic diagrams illustrating propagation of pacing pulses during delivery of a pacing therapy to both the left and right ventricles of a heart;

FIG. 6 is a schematic diagram illustrating determination of an optimal VV delay from a generated bi-ventricular pacing window.

DETAILED DESCRIPTION

Figure 1:
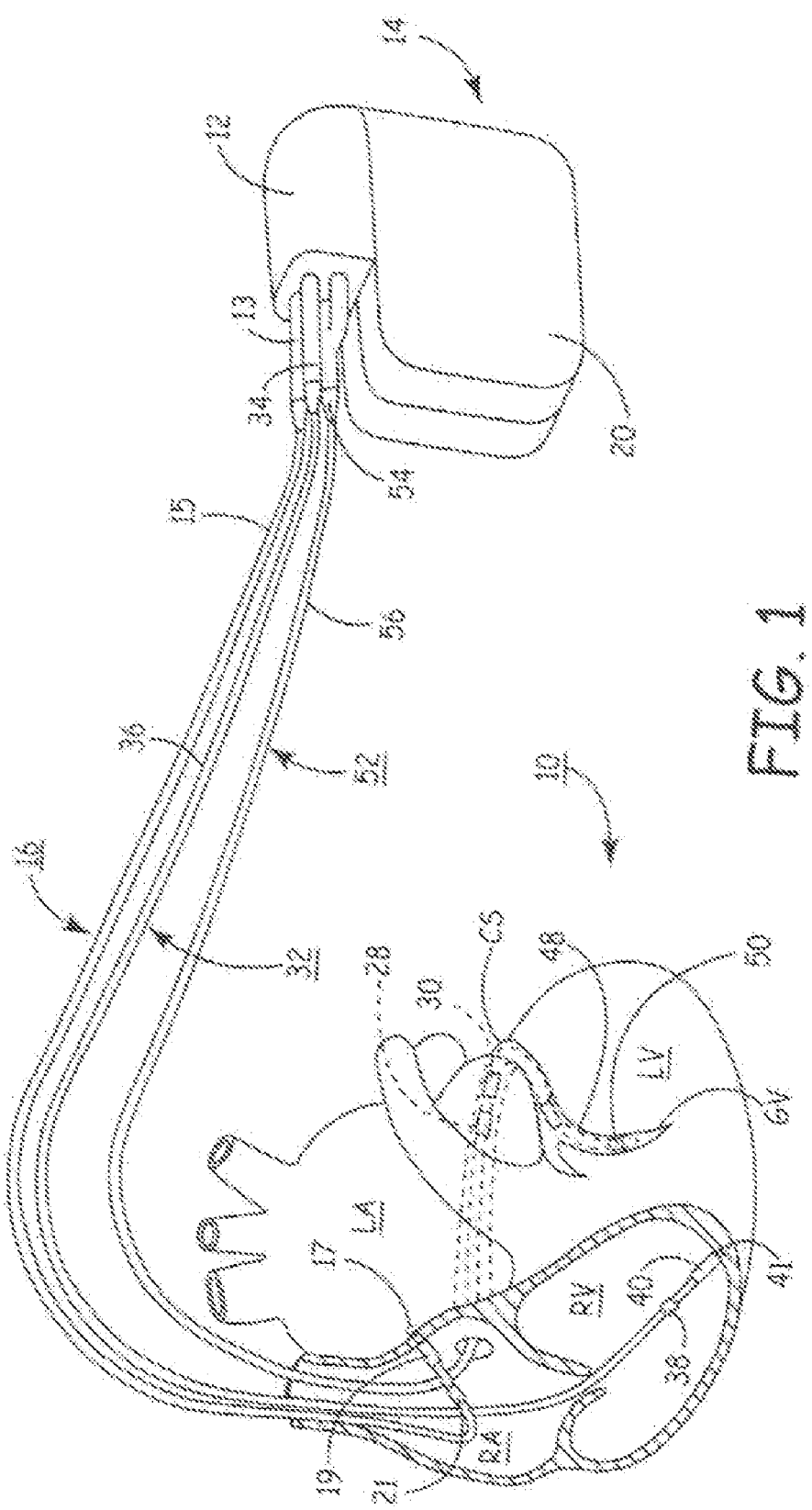
FIG. 1 is a schematic representation of an implantable medical device in which embodiments of the invention may be practiced.

FIG. 1 is a schematic representation of an implantable medical device. As illustrated in FIG. 1, embodiments of the invention may be utilized, for example, in a triple-chamber cardiac pacemaker that includes a pacemaker IPG 14 and associated leads 16, 32 and 52. The pacemaker IPG 14 is implanted subcutaneously in a patient's body between the skin and the ribs. The three endocardial leads 16, 32, and 52 operatively couple the IPG 14 with the right atrium RA, the right ventricle RV and the left ventrical LV, respectively. Each lead includes at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions, particularly sensing far field signals (e.g. far field R-waves). The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV. In addition, mechanical and/or metabolic sensors can be deployed independent of, or in tandem with, one or more of the depicted leads.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a bipolar, endocardial coronary sinus (CS) lead 52 is passed through a vein and the RA chamber of the heart 10, into the coronary sinus and then inferiorly in a branching vessel of the great cardiac vein to extend the proximal and distal LV CS pace/sense electrodes 48 and 50 alongside the LV chamber. The distal end of such a CS lead is advanced through the superior vena cava, the right atrium, the ostium of the coronary sinus, the coronary sinus, and into a coronary vein descending from the coronary sinus, such as the lateral or posteriolateral vein.

In a four chamber or channel embodiment, LV CS lead 52 bears proximal LA CS pace/sense electrodes 28 and 30 positioned along the CS lead body to lie in the larger diameter CS adjacent the LA. Typically, LV CS leads and LA CS leads do not employ any fixation mechanism and instead rely on the close confinement within these vessels to maintain the pace/sense electrode or electrodes at a desired site. The LV CS lead 52 is formed with a multiple conductor lead body 56 coupled at the proximal end connector 54 fitting into a bore of IPG connector block 12. A small diameter lead body 56 is selected in order to lodge the distal LV CS pace/sense electrode 50 deeply in a vein branching inferiorly from the great vein GV.

In this embodiment, the CS lead body 56 would encase four electrically insulated lead conductors extending proximally from the more proximal LA CS pace/sense electrode(s) and terminating in a dual bipolar connector 54. The LV CS lead body would be smaller between the LA CS pace/sense electrodes 28 and 30 and the LV CS pace/sense electrodes 48 and 50. It will be understood that LV CS lead 52 could bear a single LA CS pace/sense electrode 28 and/or a single LV CS pace/sense electrode 50 that are paired with the IND_CAN electrode 20 or the ring electrodes 21 and 38, respectively for pacing and sensing in the LA and LV, respectively.

Figure 2:
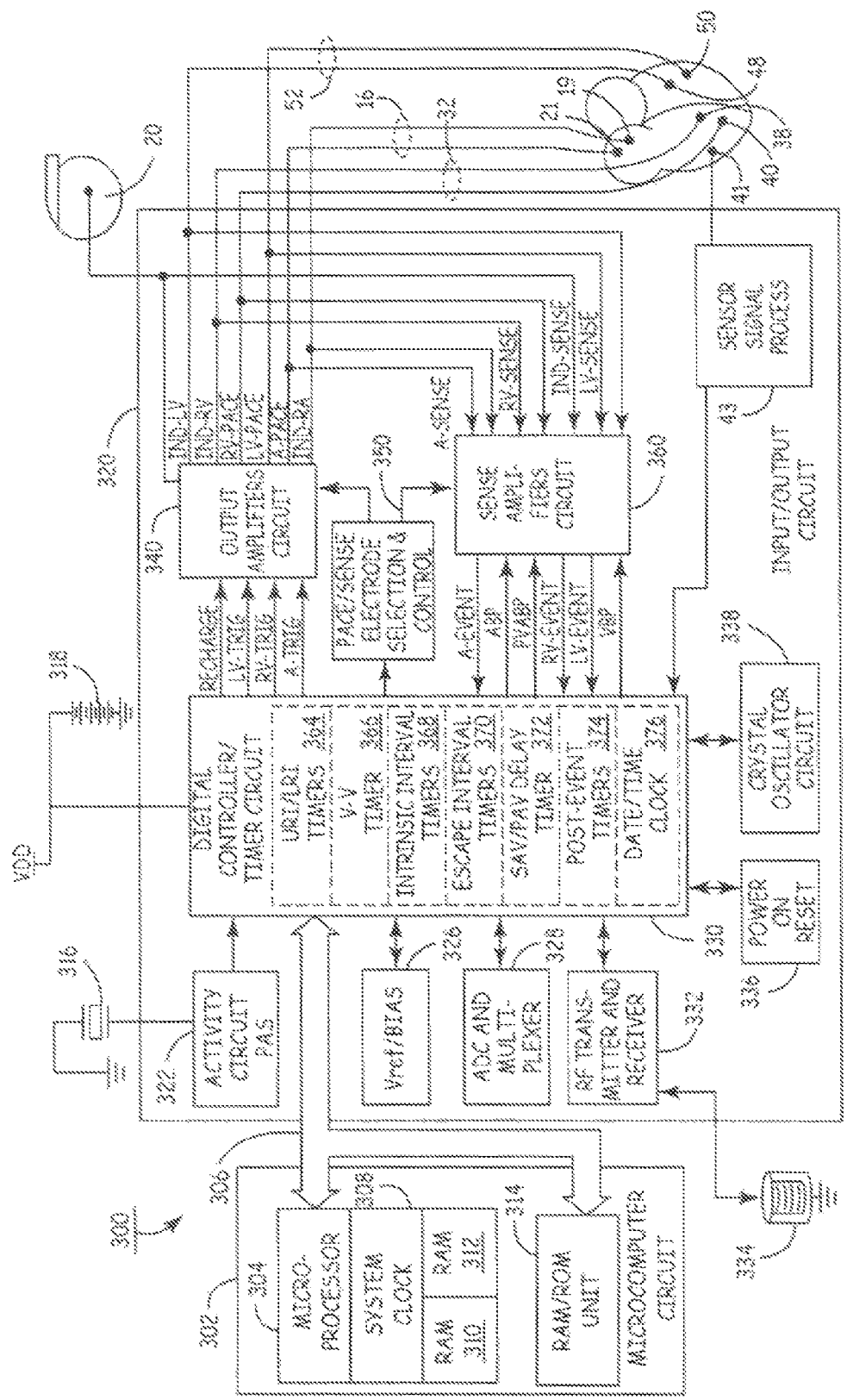
FIG. 2 is a simplified block diagram of circuitry and associated leads employed in the device FIG. 1.

FIG. 2 is a simplified block diagram of circuitry and associated leads employed in the device FIG. 1. As illustrated in FIG. 2, an implantable medical device according to one embodiment includes bipolar RA lead 16, bipolar RV lead 32, and bipolar LV CS lead 52 without the LA CS pace/sense electrodes 28 and 30 coupled with an IPG circuit 300 having programmable modes and parameters of a bi-ventricular DDDR type known in the pacing art. In addition, at least one physiologic sensor 41 is depicted operatively coupled to a portion of myocardium and electrically coupled to a sensor signal processing circuit 43. In turn the sensor signal processing circuit 43 indirectly couples to the timing circuit 330 and via bus 306 to microcomputer circuitry 302. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, the sense amplifiers circuit 360, the RF telemetry transceiver 322, the activity sensor circuit 322 as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 322 in the depicted, exemplary IPG circuit 300. The patient activity sensor 316 is coupled to the IPG housing and may take the form of a piezoelectric crystal transducer as is well known in the art and its output signal is processed and used as the RCP. Sensor 316 generates electrical signals in response to sensed physical activity that are processed by activity circuit 322 and provided to digital controller/timer circuit 330. Activity circuit 332 and associated sensor 316 may correspond to the circuitry disclosed in U.S. Pat. Nos. 5,052,388 and 4,428,378. Similarly, embodiments of the invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, embodiments of the invention may also be practiced in non-rate responsive pacemakers.

Data transmission to and from the external programmer is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. Microprocessor 304 is awakened in response to defined interrupt events, which may include A-TRIG, RV-TRIG, LV-TRIG signals generated by timers in digital timer/controller circuit 330 and A-EVENT, RV-EVENT, and LV-EVENT signals generated by sense amplifiers circuit 360, among others. The specific values of the intervals and delays timed out by digital controller/timer circuit 330 are controlled by the microcomputer circuit 302 by means of data and control bus 306 from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 304 may also serve to define variable AV delays and the uni-ventricular, pre-excitation pacing delay intervals (A-LVp) from the activity sensor data, metabolic sensor(s) and/or mechanical sensor(s). The nature of the signal utilized to optimize delivery of therapy according to the invention may include either one of a mechanical or an electrical signal. In the case of delivery being optimized in response to an electrical signal, either an electrogram from an implanted lead, an electrical signal from subcutaneously implanted electrodes, or an electrical signal from body surface electrodes may be utilized. In the case of delivery being optimized in response to a mechanical signal, a signal from a mechanical sensor incorporated into a lead or the can of the implantable pulse generator may be utilized.

In one embodiment, microprocessor 304 is a custom microprocessor adapted to fetch and execute instructions stored in RAM/ROM unit 314 in a conventional manner. It is contemplated, however, that other implementations may be suitable. For example, an off-the-shelf, commercially available microprocessor or microcontroller, or custom application-specific, hardwired logic, or state-machine type circuit may perform the functions of microprocessor 304.

Digital controller/timer circuit 330 operates under the general control of the microcomputer 302 to control timing and other functions within the pacing circuit 320 and includes a set of timing and associated logic circuits of which certain ones pertinent to the discussion are depicted. The depicted timing circuits include URI/LRI timers 364, V-V delay timer 366, intrinsic interval timers 368 for timing elapsed V-EVENT to V-EVENT intervals or V-EVENT to A-EVENT intervals or the V-V conduction interval, escape interval timers 370 for timing A-A, V-A, and/or V-V pacing escape intervals, an AV delay interval timer 372 for timing the A-LVp delay (or A-RVp delay) from a preceding A-EVENT or A-TRIG, a post-ventricular timer 374 for timing post-ventricular time periods, and a date/time clock 376.

The post-event timers 374 time out the post-ventricular time periods following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 302. The post-ventricular time periods include the PVARP, a post-atrial ventricular blanking period (PAVBP), a ventricular blanking period (VBP), and a ventricular refractory period (VRP). The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE that may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE, which may follow the V-TRIG. The microprocessor 304 also optionally calculates AV delays, post-ventricular time periods, and post-atrial time periods that vary with the sensor based escape interval established in response to the RCP(s) and/or with the intrinsic atrial rate.

The output amplifiers circuit 340 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 330 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 372 (or the V-V delay timer 366). Similarly, digital controller/timer circuit 330 generates an RA-TRIG signal that triggers output of an RA-PACE pulse (or an LA-TRIG signal that triggers output of an LA-PACE pulse, if provided) at the end of the V-A escape interval timed by escape interval timers 370.

The output amplifiers circuit 340 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 350 selects lead conductors and associated pace electrode pairs to be coupled with the atrial and ventricular output amplifiers within output amplifiers circuit 340 for accomplishing RA, LA, RV and LV pacing.

The sense amplifiers circuit 360 contains sense amplifiers corresponding to any of those presently employed in contemporary cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 controls sensitivity settings of the atrial and ventricular sense amplifiers 360.

The sense amplifiers are uncoupled from the sense electrodes during the blanking periods before, during, and after delivery of a pace pulse to any of the pace electrodes of the pacing system to avoid saturation of the sense amplifiers. The sense amplifiers circuit 360 includes blanking circuits for uncoupling the selected pairs of the lead conductors and the IND_CAN electrode 20 from the inputs of the RA sense amplifier (and LA sense amplifier if provided), RV sense amplifier and LV sense amplifier during the ABP, PVABP and VBP. The sense amplifiers circuit 360 also includes switching circuits for coupling selected sense electrode lead conductors and the IND_CAN electrode 20 to the RA sense amplifier (and LA sense amplifier if provided), RV sense amplifier and LV sense amplifier. Again, sense electrode selection and control circuit 350 selects conductors and associated sense electrode pairs to be coupled with the atrial and ventricular sense amplifiers within the output amplifiers circuit 340 and sense amplifiers circuit 360 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 330. Similarly, left atrial depolarizations or P-waves in the LA-SENSE signal that are sensed by the LA sense amplifier, if provided, result in a LA-EVENT signal that is communicated to the digital controller/timer circuit 330. Ventricular depolarizations or R-waves in the RV-SENSE signal are sensed by a ventricular sense amplifier result in an RV-EVENT signal that is communicated to the digital controller/timer circuit 330. Similarly, ventricular depolarizations or R-waves in the LV-SENSE signal are sensed by a ventricular sense amplifier result in an LV-EVENT signal that is communicated to the digital controller/timer circuit 330. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

While a triple-chamber cardiac pacemaker is described in FIGS. 1 and 2, it is understood that embodiments of the invention may also be utilized in other medical device environments, such as a subcutaneously implantable medical device for delivering pacing therapy, or a subcutaneously implantable monitoring device. An exemplary subcutaneous device is set forth in commonly assigned U.S. Patent Application No. 2007/0239053 to Bhunia, for example, incorporated herein by reference in its entirety.

Figure 3:
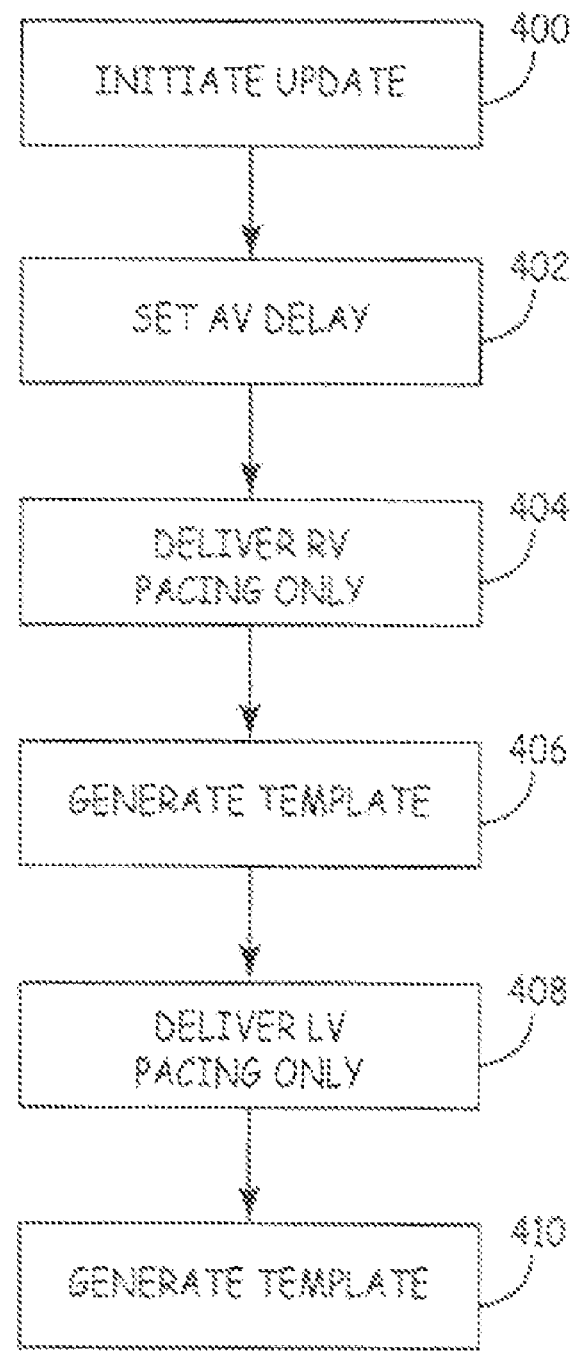
FIG. 3 is a flowchart of a method of determining a parameter for delivery of a pacing therapy.

FIG. 3 is a flowchart of a method of determining a parameter for delivery of a pacing therapy according to an embodiment. As illustrated in FIG. 3, according to an embodiment, the determination of an optimal VV delay to be utilized during delivery of a CRT pacing therapy is initiated, Block 400, either manually by the patient or a clinician, by the device at expiration of a predetermined time interval, or as a result of predetermined factors. Examples of such factors include, for example, fluid status determined by the device in response to impedance measurements generated using known impedance detection methods, heart rate exceeding a certain pre-determined value, a change in patient activity as determined by activity sensor, a change in pressure as determined by a pressure sensor, a change in cardiac function as determined by mechanical or electrical sensor.

Once the updating of the determination of the optimal VV delay is initiated, the device sets the AV delay to a predetermined value that ensures that the morphology of subsequently sensed QRS wave patterns occur as the result of the delivery of pacing pulses by the device, Block 402. According to an embodiment, the microprocessor 304 sets the AV delay in the controller/timing circuit 330 as 80 ms, for example. Control circuit 350 then selects lead conductors and associated pace/sense electrode pairs so that pacing pulses are temporarily delivered in only the right ventricle, Block 404, and a template is then generated for the right ventricle only delivered pacing based on a sensed QRS morphology resulting from the delivered pacing pulses, Block 406, which is then stored by the device. Similarly, control circuit 350 selects lead conductors and associated pace/sense electrode pairs so that pacing pulses are temporarily delivered in only the left ventricle, Block 408, and a template is generated for the left ventricle only delivered pacing based on a resulting sensed QRS morphology, Block 410. The template generated for the right ventricle only delivered pacing generated in Block 406 and for the left ventricle only delivered pacing generated in Block 410 are then utilized to adjust delivery of a CRT pacing therapy, as described below.

FIGS. 4A to 4C are schematic diagrams illustrating propagation of pacing pulses during delivery of a pacing therapy to both the left and right ventricles of a heart. In order to determine the optimal VV delay necessary to most effectively deliver the pacing therapy for achieving maximal electrical synchrony of the left ventricle, the degree to which the LV and RV pacing pulses contribute to left ventricle electrical activation must be determined. This contribution distribution between the two ventricles will affect the desired timing between the delivery of pacing pulses to the right and left ventricle.

The propagation of pacing pulses from the delivery site of the associated electrode, through the myocardium of the corresponding ventricle will be dependent upon multiple factors, such as the location of the electrodes, and the integrity of the myocardium around the electrodes and within the associated propagation pathway through the ventricle. At extreme ends of the VV delay settings, the QRS morphology will more closely reflect activation from the first paced ventricular lead. As illustrated in FIG. 4A, if right ventricular pacing RVP is delivered first, and the amount of time before the delivery of left ventricular pacing LVP is too great, the excitation 450 resulting from the right ventricular pacing RVP will be greater than the excitation 452 resulting from the left ventricular pacing LVP. Similarly, as illustrated in FIG. 4B, if left ventricular pacing LVP is delivered first, and the amount of time before the delivery of right ventricular pacing RVP is too great, the excitation 454 resulting from the left ventricular pacing LVP will be greater than the excitation 456 resulting from the right ventricular pacing RVP. As illustrated in FIG. 4C, since optimal VV delay would result in equal amounts of the myocardium of the ventricle being activated by both of the delivered pacing pulses, it is desirable for the VV delay to be adjusted so that no matter if the right ventricle or the left ventricle is paced first, the excitation 458 resulting from the left ventricular pacing LVP will be approximately equal to the excitation 460 resulting from the right ventricular pacing RVP, so that the amount of myocardium being activated in both chambers is approximately equal.

Figure 5:
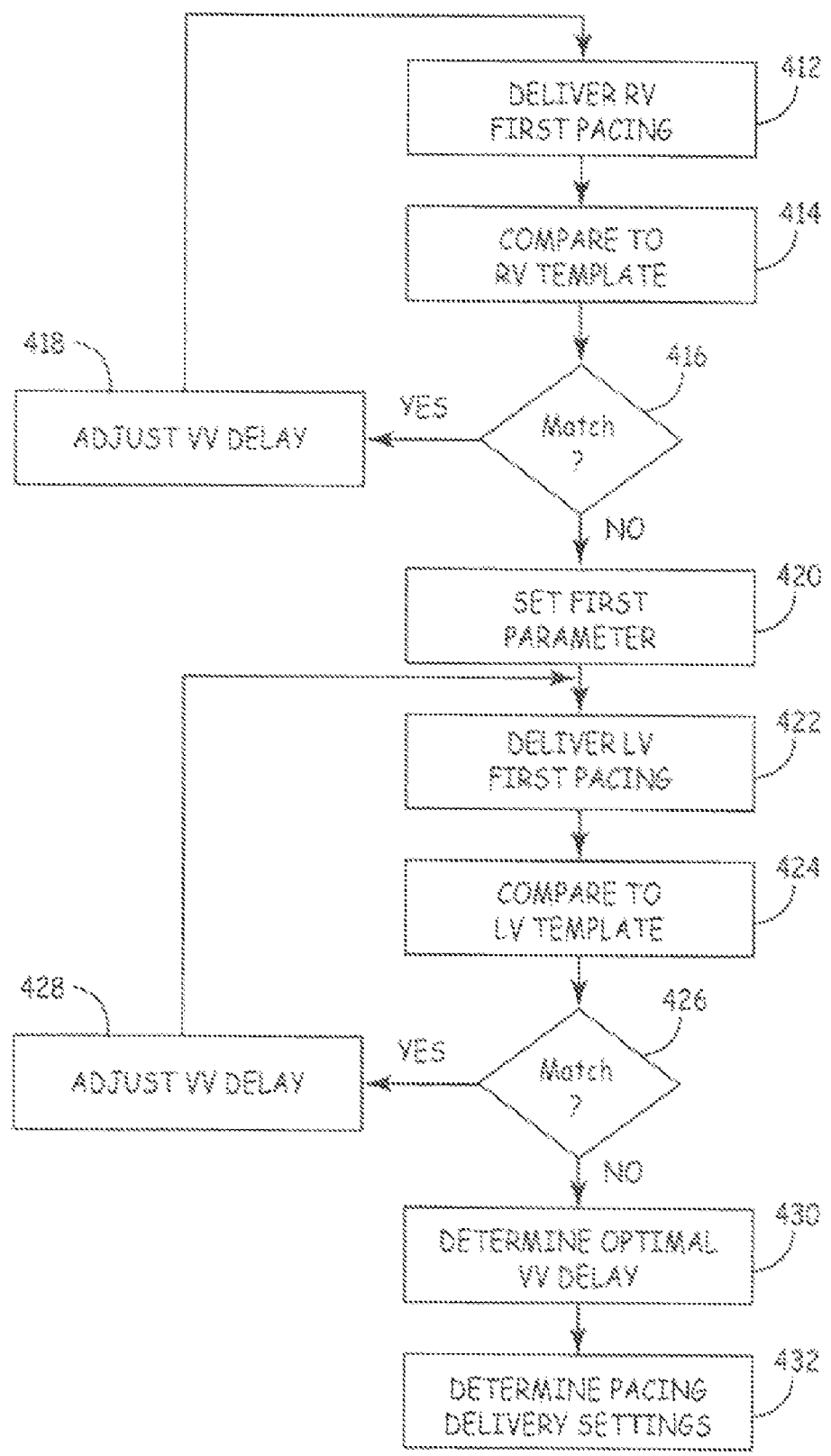
FIG. 5 is a flowchart of a method of determining a parameter for delivery of a pacing therapy.

FIG. 5 is a flowchart of a method of determining a parameter for delivery of a pacing therapy according to an embodiment. As illustrated in FIG. 5, for example, once the RV template has been determined, the device delivers pacing pulses so that pacing is delivered in the right ventricle first, Block 412. For example, the pacing pulses are initially delivered so as to correspond to a bi-ventricular pacing scheme in which the right ventricular pacing occurs first, followed by left ventricular pacing being delivered 80 ms after each delivered right ventricular pacing pulse. The resulting QRS morphology is then compared to the previously generated RV template (FIG. 3), Block 414, and a determination is made as to whether the resulting QRS morphology matches the RV template, Block 416. The determination as to whether the resulting QRS morphology matches the RV template, Block 416, can be made using known template matching methods, such as the wavelet percent matching described in U.S. Pat. No. 6,393,316 to Gillberg et al., for example, incorporated herein by reference in its entirety. In particular, for example, the device stores digitized depolarization signals associated with subsequently delivered pacing therapy to the right ventricle, and transforms the digitized signal into signal wavelet coefficients. Signal wavelet coefficients having higher amplitudes are then identified, and a match metric is generated corresponding to the wavelet coefficients having a higher amplitude and a corresponding set of wavelet coefficients derived from the depolarization signal forming the RV template.

If the QRS morphology matches the RV template within a predetermined threshold, Yes in Block 416, such as being greater than a 70% match, for example, the device reduces the VV delay (e.g., VV delay now becomes pacing delivered first in the right ventricle by 60 ms), Block 418, and again delivers pacing pulses, Block 412, using the updated rate. For example, according to one embodiment, the device adjusts the VV delay in 20 ms increments so that the rate would initially be reduced from 80 ms to 60 ms. The resulting QRS morphology is then compared to the RV template, Block 414, and the process is repeated. As long as the QRS morphology continues to match the template within the predetermined threshold, Yes in Block 416, indicating the QRS morphology corresponds to a predominantly RV-paced QRS morphology, the device continues to adjust the VV delay, 418. Once the resulting QRS morphology no longer matches the RV template within the predetermined threshold, No in Block 416, the VV delay associated with the non-matching QRS morphology is set as the first parameter that will subsequently be utilized to determine the optimal VV delay, Block 420.

Similarly, once the LV template has been determined, the device delivers pacing pulses so that pulses are delivered in the left ventricle first, Block 422. For example, the pacing pulses are initially delivered so as to correspond to a bi-ventricular pacing scheme in which the left ventricular pacing occurs first, followed by right ventricular pacing being delivered 80 ms after each delivered left ventricular pacing pulse. The resulting QRS morphology is then compared to the previously generated LV template (FIG. 3), Block 424, and a determination is made as to whether the resulting QRS morphology matches the LV template, Block 426. The determination as to whether the resulting QRS morphology matches the LV template, Block 426, can be made using known template matching methods, such as the wavelet percent matching described in U.S. Pat. No. 6,393,316 to Gillberg et al., for example, incorporated herein by reference in its entirety. In particular, for example, the device stores digitized depolarization signals associated with subsequently delivered pacing therapy to the left ventricle, and transforms the digitized signal into signal wavelet coefficients. Signal wavelet coefficients having higher amplitudes are then identified, and a match metric is generated corresponding to the wavelet coefficients having a higher amplitude and a corresponding set of wavelet coefficients derived from the depolarization signal forming the LV template.

If the QRS morphology matches the LV template within a predetermined threshold, Yes in Block 426, such as being greater than a 50% match, for example, the device adjusts the VV delay, Block 428, and again delivers pacing pulses in only the left ventricle, Block 422, using the updated VV delay. For example, according to one embodiment, the device adjusts the VV delay in 20 ms increments so that the VV delay would initially be reduced from 80 ms to 60 ms. The resulting QRS morphology is then compared to the LV template, Block 424, and the process is repeated. As long as the QRS morphology continues to match the template within the predetermined threshold, Yes in Block 426, indicating the QRS morphology corresponds to a predominantly LV-paced QRS morphology, the device continues to adjust the VV delay, 428. Once the resulting QRS morphology no longer matches the LV template within the predetermined threshold, No in Block 426, the VV delay associated with the non-matching QRS morphology is set as the second parameter that will subsequently be used to determine the optimal VV delay, Block 430.

According to another embodiment, the initial VV delay for delivering pacing pulses could be set at the lower end of the pacing, such as zero, for example, and the VV delay would then be adjusted in Blocks 418 and 428 by being increased by a predetermined amount, such as 20 ms, for example.

According to an embodiment, the device defines the optimal VV delay, Block 432, as being within a bi-ventricular pacing window defined by the first and second parameters generated in Blocks 420 and 430, respectively. For example, according to one embodiment, the first parameter associated with the right ventricular pacing, Block 420, is set as the beginning of the bi-ventricular pacing window and second parameter associated with the left ventricular pacing, Block 430, is set as the end of the bi-ventricular pacing window. The device then sets the optimal VV delay as a value within the bi-ventricular pacing window, such as the midpoint of the bi-ventricular pacing window, for example.

FIG. 6 is a schematic diagram illustrating determination of an optimal VV delay from a generated bi-ventricular pacing window according to an embodiment. For example, as illustrated in FIG. 6, if the first parameter is set as 60 ms, i.e., the first non-matching QRS complex during delivery of right ventricular pacing first occurred when the VV delay was adjusted to 60 ms, and the second parameter is set as 20 ms, i.e., the first non-matching QRS complex during delivery of left ventricular pacing first occurred when the VV delay was adjusted to 20 ms, the determined bi-ventricular window 600 extends between a bi-ventricular pacing regimen in which the right ventricle is paced first, with the left ventricle being paced 60 ms subsequent to the right ventricular being paced, and a bi-ventricular pacing regimen in which the left ventricle is paced first, with the right ventricle being paced 20 ms subsequent to the left ventricular being paced. The optimal VV delay is then set as the midway point 602 of the bi-ventricular pacing window 600, i.e., the right ventricle being paced first and the left ventricle being paced 20 ms after the right ventricular being paced. The device then delivers bi-ventricular pacing therapy using the determined optimal VV delay.

Figure 7:
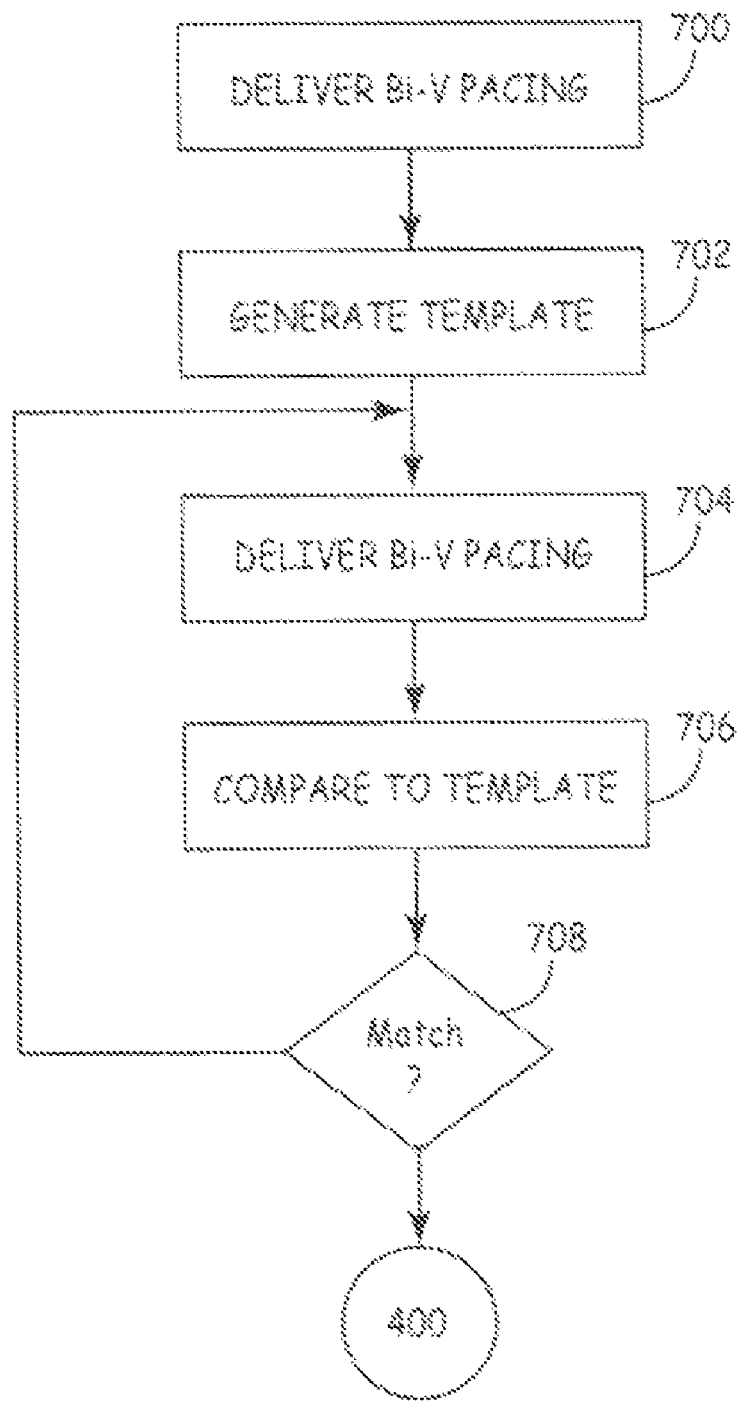
FIG. 7 is a flowchart of a method of determining a parameter for delivery of a pacing therapy.

FIG. 7 is a flowchart of a method of determining a parameter for delivery of a pacing therapy. As illustrated in FIG. 7, for example, once the optimal VV delay has been determined in Block 432 of FIG. 5, the device delivers the bi-ventricular pacing therapy using the determined optimal VV delay, Block 700, and generates a corresponding Bi-V template in response to the delivered therapy, Block 702, using known template generation techniques. The bi-ventricular pacing therapy subsequently delivered is then compared to the Bi-V template, Block 704, and a determination is made as to whether a QRS morphology resulting from the delivered bi-ventricular pacing therapy matches the Bi-V template within a predetermined threshold, Block 708, using known template matching methods, such as the wavelet percent matching described in U.S. Pat. No. 6,393,316 to Gillberg et al., for example, incorporated herein by reference in its entirety. In particular, for example, the device stores digitized depolarization signals associated with subsequently delivered bi-ventricular pacing therapy, and transforms the digitized signal into signal wavelet coefficients. Signal wavelet coefficients having higher amplitudes are then identified, and a match metric is generated corresponding to the wavelet coefficients having a higher amplitude and a corresponding set of wavelet coefficients derived from the depolarization signal forming the Bi-V template.

If the resulting QRS morphology matches the Bi-V template within a predetermined threshold, Yes in Block 708, such as being greater than a 70% match, for example, bi-ventricular pacing continues to be delivered by the device using the previously determined optimal VV delay. However, once the resulting QRS morphology no longer matches the Bi-V template within the predetermined threshold, No in Block 708, the updating of the optimal VV delay is initiated, Block 400, so that a new optimal VV delay is determined.

According to an embodiment, if, during the determination of either the first and second parameters, Block 412-416 and 418, and Blocks 422-426 and 428, the morphology of subsequent delivered pacing pulse fails to not match the corresponding threshold, i.e., does not correspond to something other than a predominantly RV-paced morphology or a predominantly LV-paced morphology, the associated first and/or second parameter is set in Block 420 and/or 430 as the highest rate delivered in Block 412 or Block 422, i.e., 80 ms for example. In addition, if the patient is determined to be in an atrial fibrillation (AF) event, made using known AF detection methods, the optimal VV delay os determined, as described above, however deliver of the bi-ventricular pacing therapy is temporarily withheld during the AF event.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

We claim:

1. A medical device for determining a parameter for delivery of a predetermined pacing therapy, comprising:
a plurality of electrodes to deliver a pacing therapy, including the predetermined pacing therapy;
a control unit operatively coupled with the plurality of electrodes for controlling the timing of the delivery of the pacing therapy, including the predetermined pacing therapy, by the electrodes; and
a processor to generate a first template in response to the pacing therapy being delivered to only one of a right ventricle and a left ventricle, and a second template in response to the pacing therapy being delivered to only the other of the right ventricle and the left ventricle, wherein the processor determines the parameter in response to a comparing of subsequently delivered pacing therapy to the first template and the second template;
wherein the processor adjusts a timing between delivery of pacing therapy to one of the first ventricle and the second ventricle and the other of the first ventricle and the second ventricle in response to the comparing.

2. The device of claim 1, wherein one of the first template and the second template corresponds to a predominantly right ventricular-paced morphology, and the other of the first template and the second template corresponds to a predominantly left ventricular-paced morphology.

3. The device of claim 1, wherein the processor reduces the timing in response to delivered pacing therapy not matching one of the first template and the second template within a predetermined threshold.

4. The device of claim 1, wherein the processor defines a parameter window in response to timing of pacing therapy delivered in the right ventricle that does not match the first template within a predetermined threshold, and timing of pacing therapy delivered in the left ventricle that does not match the second template within the predetermined threshold.

5. The device of claim 4, wherein the processor determines the parameter as being a midpoint of the parameter window.

6. The device of claim 1, wherein the processor compares the subsequent delivery of the pacing therapy to the first template and the second template using wavelet percent matching.

7. A medical device for determining a parameter for delivery of a predetermined pacing therapy, comprising:
a plurality of electrodes to deliver a pacing therapy, including the predetermined pacing therapy;
a control unit controlling the timing of the delivery of the pacing therapy, including the predetermined pacing therapy, by the electrodes; and
a processor to generate a first template in response to the pacing therapy being delivered to only one of a right ventricle and a left ventricle, and a second template in response to the pacing therapy being delivered to only the other of the right ventricle and the left ventricle, wherein the processor determines the parameter in response to a comparing of subsequently delivery of the pacing therapy to the first template and the second template, generates a third template in response to delivery of the predetermined pacing therapy delivered corresponding to the defined parameter, and updates the parameter in response to a comparing of the delivered predetermined pacing therapy and the third template;
wherein the processor adjusts a timing between delivery of the pacing therapy to one of the first ventricle and the second ventricle and the other of the first ventricle and the second ventricle in response to the comparing.

8. The device of claim 7, wherein one of the first template and the second template corresponds to a predominantly right ventricular-paced morphology, and the other of the first template and the second template corresponds to a predominantly left ventricular-paced morphology.

9. The device of claim 7, wherein the processor reduces the timing in response to delivered pacing therapy not matching one of the first template and the second template within a predetermined threshold.

10. The device of claim 7, wherein the processor defines a parameter window in response to timing of pacing therapy delivered in the right ventricle that does not match the first template within a predetermined threshold, and timing of pacing therapy delivered in the left ventricle that does not match the second template within the predetermined threshold.

11. The device of claim 10, wherein the processor determines the parameter as being a midpoint of the parameter window.

12. The device of claim 7, wherein the processor compares the subsequently delivered pacing therapy to the first template and the second template using wavelet percent matching.

13. A method of delivery of a predetermined pacing therapy, comprising:
  delivery of a pacing therapy to a patient, including the predetermined pacing therapy;
  generating a first template in response to pacing therapy other than the predetermined pacing therapy being delivered to only one of a right ventricle and a left ventricle, and a second template in response to pacing therapy other than the predetermined pacing therapy being delivered to only the other of the right ventricle and the left ventricle; and
  determining the parameter in response to a comparing of subsequently delivered pacing therapy to the first template and the second template; and
    adjusting a timing between delivery of the pacing therapy to one of the first ventricle and the second ventricle and the other of the first ventricle and the second ventricle in response to the comparing; and
  delivering the pacing therapy using the adjusted timing.

14. The method of claim 13, wherein one of the first template and the second template corresponds to a predominantly right ventricular-paced morphology, and the other of the first template and the second template corresponds to a predominantly left ventricular-paced morphology.

15. The method of claim 13, further comprising reducing the timing in response to delivered pacing therapy not matching one of the first template and the second template within a predetermined threshold.

16. The method of claim 13, further comprising defining a parameter window in response to timing of pacing therapy delivered in the right ventricle that does not match the first template within a predetermined threshold, and timing of pacing therapy delivered in the left ventricle that does not match the second template within the predetermined threshold.

17. The method of claim 16, further comprising determining the parameter as being a midpoint of the parameter window.

18. The method of claim 13, further comprising comparing the subsequently delivered pacing therapy to the first template and the second template using wavelet percent matching.

19. The method of claim 13, further comprising:
  generating a third template in response to delivery of the predetermined pacing therapy delivered corresponding to the defined parameter; and
  updating the parameter in response to a comparing of the delivered predetermined pacing therapy and the third template.

20. The method of claim 19, wherein generating the third template comprises:
  storing a first digitized depolarization signal associated with delivery of the predetermined pacing therapy;
  transforming the stored first digitized depolarization signal into signal wavelet coefficients;
  storing a second digitized depolarization signal associated with generating of the third template;
  transforming the stored first digitized depolarization signal into first signal wavelet coefficients and the stored second digitized depolarization signal into second signal wavelet coefficients;
  determining first signal wavelet coefficients having higher amplitudes; and
  generating a match metric in response to the first signal wavelet coefficients having higher amplitudes and the second signal wavelet coefficients.

* * * * *